(12) United States Patent
Boegeman et al.

(10) Patent No.: US 10,155,125 B2
(45) Date of Patent: Dec. 18, 2018

(54) REVERSE LOOP ABLATION DEVICE

(71) Applicant: Lake Region Manufacturing, Inc., Chaska, MN (US)

(72) Inventors: James Allan Boegeman, Shakopee, MN (US); Brian Michael Moyer, Hutchinson, MN (US); Paul James McCormick, III, Hutchinson, MN (US)

(73) Assignee: Lake Region Manufacturing, Inc., Chaska, MN (US)

( * ) Notice: Subject to any disclaimer, the term of this patent is extended or adjusted under 35 U.S.C. 154(b) by 503 days.

(21) Appl. No.: 14/787,528

(22) PCT Filed: Apr. 30, 2014

(86) PCT No.: PCT/US2014/036185
§ 371 (c)(1),
(2) Date: Oct. 28, 2015

(87) PCT Pub. No.: WO2014/179471
PCT Pub. Date: Nov. 6, 2014

(65) Prior Publication Data
US 2016/0067528 A1    Mar. 10, 2016

Related U.S. Application Data

(60) Provisional application No. 61/817,433, filed on Apr. 30, 2013.

(51) Int. Cl.
*A61B 18/12* (2006.01)
*A61N 7/02* (2006.01)
*A61B 18/14* (2006.01)
*A61B 5/0408* (2006.01)
*A61B 18/00* (2006.01)
*A61N 7/00* (2006.01)

(52) U.S. Cl.
CPC ............ *A61N 7/022* (2013.01); *A61B 5/0408* (2013.01); *A61B 18/1492* (2013.01); *A61B 2018/0022* (2013.01); *A61B 2018/00357* (2013.01); *A61B 2018/00375* (2013.01); *A61B 2018/00577* (2013.01); *A61B 2018/00839* (2013.01); *A61N 2007/003* (2013.01); *A61N 2007/0069* (2013.01)

(58) Field of Classification Search
CPC ........ A61B 18/1492; A61B 2018/0022; A61B 2018/00357; A61B 2018/00375; A61B 2018/00577; A61B 2018/00839; A61B 5/0408; A61N 2007/0033; A61N 2007/0069; A61N 7/022
See application file for complete search history.

(56) References Cited

U.S. PATENT DOCUMENTS

| 8,216,216 | B2 | 7/2012 | Warnking et al. |
| 8,380,275 | B2 | 2/2013 | Kim et al. |
| 8,398,623 | B2 | 3/2013 | Warnking et al. |
| 2002/0177765 | A1 | 11/2002 | Bowe et al. |
| 2003/0073891 | A1 | 4/2003 | Chen et al. |

(Continued)

OTHER PUBLICATIONS

International PCT Search Report, PCT/US2014/036185, dated Feb. 23, 2016.

*Primary Examiner* — Daniel Fowler
(74) *Attorney, Agent, or Firm* — Michael F. Scalise

(57) ABSTRACT

The present invention relates to apparatus and methods for cardiac ablation and to sensor structures useful in such apparatus and methods.

23 Claims, 9 Drawing Sheets

(56) References Cited

U.S. PATENT DOCUMENTS

| | | | |
|---|---|---|---|
| 2004/0019349 A1 | 1/2004 | Fuimaono et al. | |
| 2005/0187455 A1* | 8/2005 | Rashidi | A61B 18/1492 600/374 |
| 2005/0288626 A1* | 12/2005 | Koerner | A61M 25/0136 604/95.04 |
| 2006/0036218 A1* | 2/2006 | Goodson, IV | A61M 25/0054 604/264 |
| 2008/0249518 A1* | 10/2008 | Warnking | A61N 7/022 606/27 |
| 2012/0130366 A1* | 5/2012 | Carroll | A61B 18/1492 606/41 |

\* cited by examiner

FIG. 3
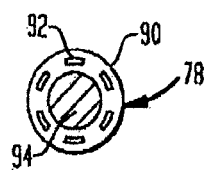
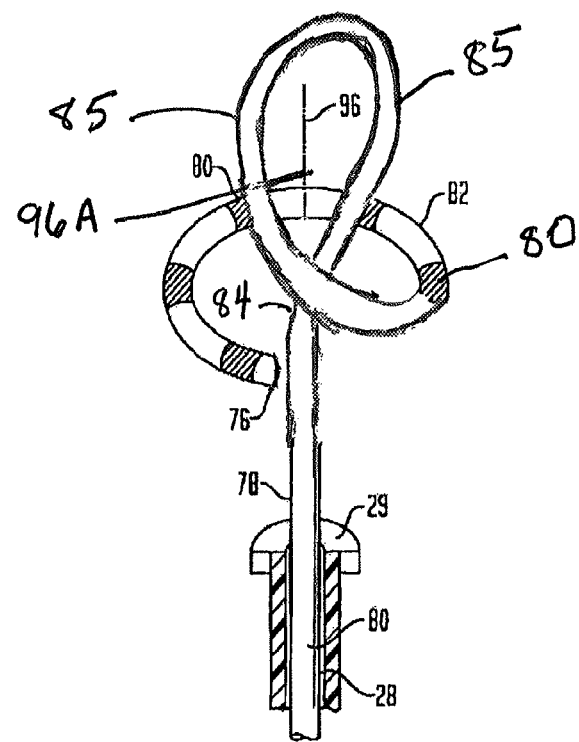
FIG. 4

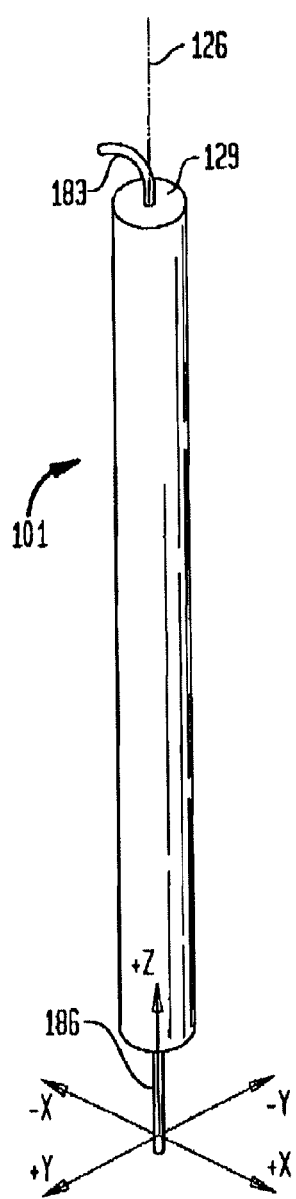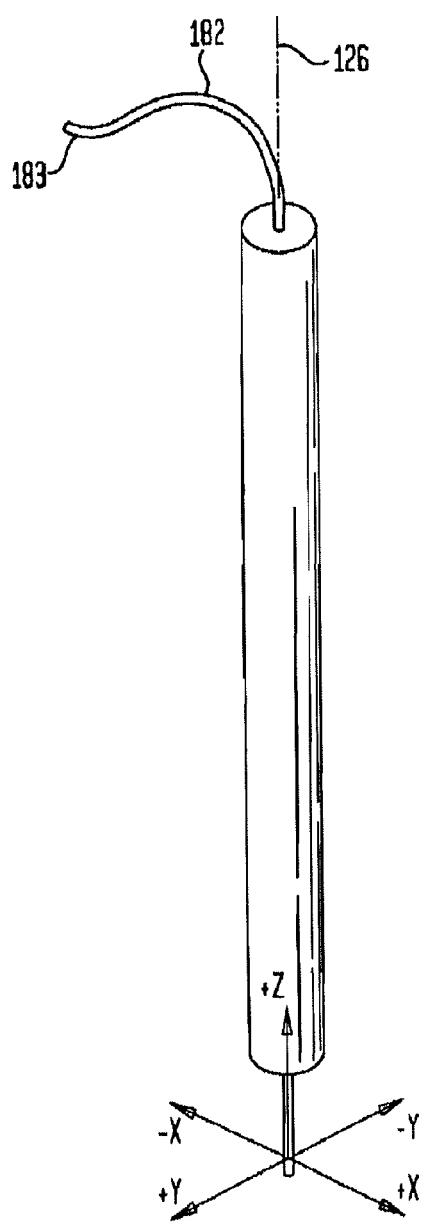

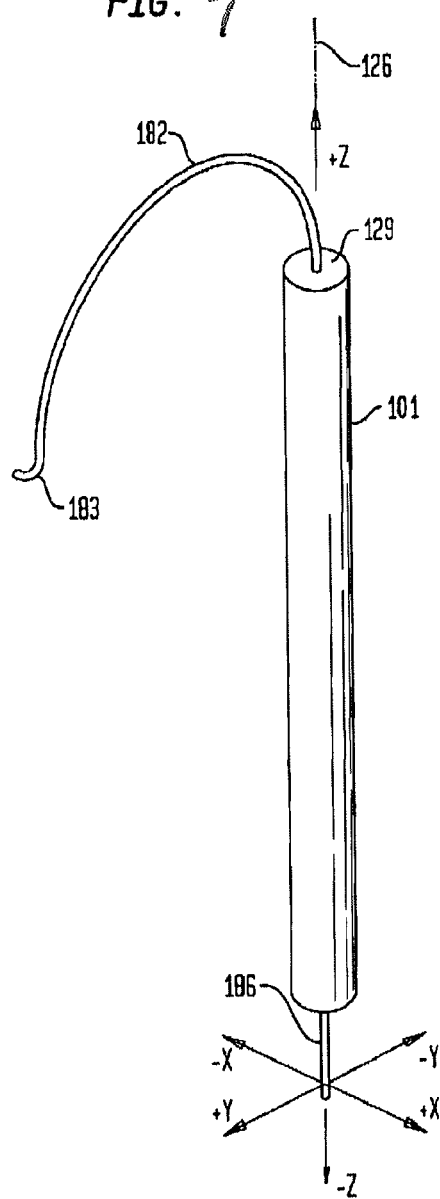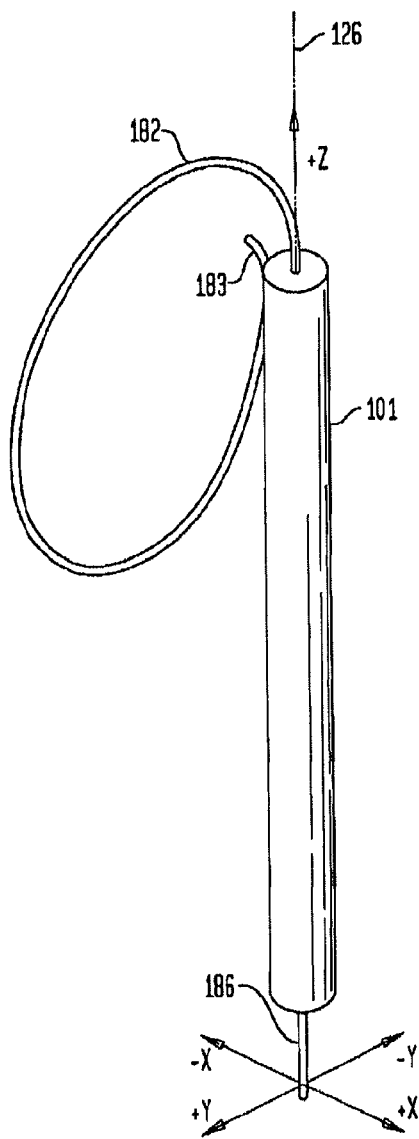

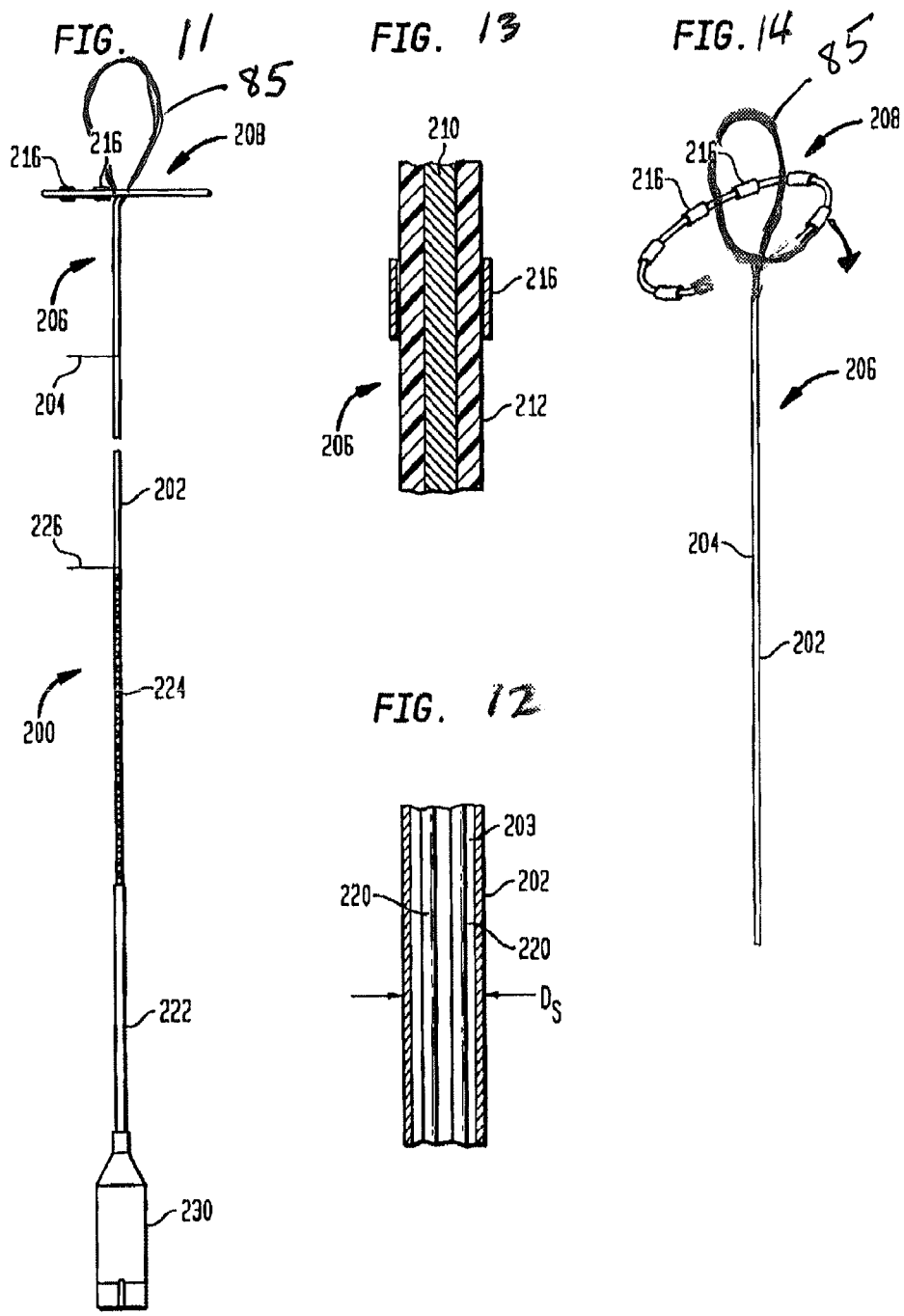

REVERSE LOOP ABLATION DEVICE

CROSS REFERENCE TO RELATED APPLICATIONS

This application claims priority from U.S. provisional patent application Ser. No. 61/817,433 filed Apr. 30, 2013, the teachings of which are incorporated by reference herein.

BACKGROUND

The present invention relates to apparatus and methods for cardiac ablation and to sensor structures useful in such apparatus and methods.

Contraction or "beating" of the heart is controlled by electrical impulses generated at nodes within the heart and transmitted along conductive pathways extending within the wall of the heart. Certain diseases of the heart known as cardiac arrhythmias involve abnormal generation or conduction of the electrical impulses. One such arrhythmia is atrial fibrillation or "AF." Certain cardiac arrhythmias can be treated by deliberately damaging the tissue along a path crossing a route of abnormal conduction, either by surgically cutting the tissue or by applying energy or chemicals to the tissue, so as to form scar. The scar blocks the abnormal conduction and thereby reduces or eliminates AF. For example, in treatment of AF, it has been proposed to ablate tissue in a partial or complete loop around a pulmonary vein within the vein itself, within the ostium or opening connecting the vein to the heart, or within the wall of the heart surrounding the ostium. It would be desirable to perform such ablation using a catheter-based device which can be advanced into the heart through the patient's circulatory system. Despite all efforts in the art, however, still further improvement would be desirable.

BRIEF SUMMARY OF THE INVENTION

Briefly, in one aspect, the present invention provides apparatus for cardiac treatment which includes a catheter having proximal and distal ends and a lumen, as well as an expansible ablation device mounted at or near the distal end of the catheter. The ablation device has a collapsed condition and an expanded condition, and is operative to apply energy to cardiac tissues in proximity to the device when the device is in the expanded condition. In its expanded condition, the device and catheter define a port open to the exterior of the expansible ablation device on the distal side of the device. Desirably, the ablation device defines a bore or lumen extending through the ablation device. The bore has a first end communicating with the lumen and a second end defining the port.

An apparatus according to this invention optionally also includes an elongated sensor probe which also has proximal and distal ends. The sensor probe includes one or more electrodes disposed adjacent the distal end of the sensor probe. The lumen and the ablation device are constructed and arranged so that the sensor probe can be removably positioned in the passageway, with the distal end of the sensor probe projecting out of the ablation device through the port.

The ablation device may be arranged to direct energy into a loop-like ablation region which encircles the port. Most preferably, the expansible ablation device includes an ultrasonic emitter and an expansible energy-directing structure, such as a balloon structure, adapted to direct ultrasonic energy from the emitter into the loop-like region when the expansible ablation device is in its expanded condition.

The expansible inflation device desirably defines a forward-to-rearward axis, and the loop-like ablation region has an axis substantially coaxial with this forward-to-rearward axis. Desirably, the port is disposed on or adjacent to the forward-to-rearward axis of the ablation device, and the sensor probe includes a distal region carrying the electrode or electrodes. The distal region projects from the port when the sensor probe is positioned in the lumen of the catheter and the bore of the ablation device. Desirably, the sensor probe is constructed and arranged so that the distal region tends to form a hoop when the distal region projects from the port. The hoop desirably encircles the forward-to-rearward axis, and may be substantially coaxial with the forward-to-rearward axis and with the loop-like ablation region.

As further discussed below, apparatus according to this aspect of the invention allows the physician to position the expansible ablation structure as desired as, for example, to form a ring-like lesion. However, once the ablation device has been positioned, the sensor probe can be introduced readily through the passageway and is automatically aligned with the area to be ablated. For example, where the apparatus is used to form a ring-like lesion around a pulmonary vein or pulmonary vein ostium, the sensor probe will automatically be placed in alignment with the lesion and in alignment with the pulmonary vein and pulmonary vein ostium when it is introduced through the lumen and bore. Depending upon the radius of the hoop formed by the sensor, the hoop may be disposed inside the lesion to monitor electrical activity within the area enclosed or to be enclosed by the lesion. Alternatively, where the radius of the hoop formed by the sensing probe exceeds the radius of the ablation region, the hoop will lie outside of the ablation region, and will monitor electrical activity in this region.

The removable sensor probe does not impede other procedures such as introduction of a contrast medium through the passageway during positioning. The sensor probe can be placed at any time during the procedure to monitor electrical activity before or after ablation, or even during ablation. Because the catheter and ablation device serve as an introducer structure for the sensor probe, the sensor probe can be introduced readily, without interrupting the procedure. Moreover, because the sensor probe is removable, the apparatus may include more than one sensor probe, which may have different configurations and different sizes, so that the sensing electrodes can be placed at different locations.

A further aspect of the invention provides methods of cardiac ablation which include the steps of advancing an apparatus including a catheter and an expansible ablation device into the subject while the ablation device is in a collapsed condition, until the ablation device is disposed in a chamber of the subject heart, and then expanding the ablation device to an expanded condition. In a method according to this aspect of the invention, the ablation device is positioned in a desired disposition relative to the heart and actuated to apply energy in a loop-like region, having a predetermined spatial relationship to the ablation device, and thereby ablate the tissue in this region so as to form a lesion.

Methods according to the invention desirably further include the step of advancing a sensing probe through a continuous passageway from the proximal end of the catheter through the ablation device, so that a distal region of the sensing probe projects out of a port on the ablation device and contacts tissue of the subject adjacent the ablation device. In methods according to this aspect of the invention, the ablation device desirably at least partially positions the projecting distal region of the sensing probe relative to the heart. The method desirably further includes the step of detecting electrical signals in the subject using the sensing probe. Methods according to this aspect of the invention afford advantages similar to those discussed above in connection with the apparatus.

Yet another aspect of the invention provides a probe which includes a probe body having an undeployed condition and a deployed condition, and one or more functional elements such as electrodes carried on the probe body. The probe body, in its undeployed condition, desirably is elongated and flexible, and desirably includes a distal region carrying the functional elements. In its deployed condition, the probe body includes a base portion extending in a distal direction, and a limb extending from the distal end of the base portion in a radial direction transverse to the distal direction. The limb also extends in a proximal direction opposite to the distal direction. The limb has an outer end remote from the base portion. In the deployed condition, the probe body desirably also forms a hoop extending from the outer end of the limb, at least partially around the base portion. The hoop desirably carries one or more of the functional elements.

A probe according to this aspect of the invention desirably is used in combination with an introducer structure having proximal and distal ends and a port adjacent the distal end of the introducer structure, as well as a passageway extending from adjacent the proximal end to the port. The probe body in its undeployed condition desirably is slideable in the passageway. In the deployed condition, the base portion of the probe body extends in the passageway and projects from the port. The introducer structure may include a catheter and an expansible ablation device as discussed above. The ablation device, in its expanded condition, may define a distal wall, and the port may be disposed on or forward of the distal wall. The ablation device may have a projection extending forwardly from the distal wall when the ablation device is in the expanded condition, and the port may be disposed on this projection. When the sensor probe is in its deployed condition, the base portion projects out of the port forward of the distal wall, whereas the limb portion extends rearwardly towards the distal wall, and the hoop region overlies the distal wall and extends around the projection. Stated another way, in the deployed condition, the sensor probe extends out of the port and rearwardly towards the distal wall, so as to place the hoop region in proximity to or abutting the distal wall of the ablation device. Desirably, the probe body is a self-deploying resilient structure which is arranged to form the configuration including the limb and hoop region spontaneously, under the influence of its own resilience, as the distal end of the probe body is advanced outwardly through the port.

These and other objects, features and advantages of the present invention will be more readily apparent from the detailed description of the preferred embodiments set forth below, taken in conjunction with the accompanying drawings.

BRIEF DESCRIPTION OF THE DRAWINGS

FIG. 3 is a diagrammatic sectional view taken along line 3-3 in FIG. 2.

FIG. 4 is a diagrammatic perspective view of a reverse loop ablation device of this invention.

FIGS. 5-10 are schematic perspective views depicting portions of the apparatus shown in FIG. 4 during successive stages of deployment.

FIG. 11 is a diagrammatic elevational view of a probe in accordance with a further embodiment of the invention.

FIG. 12 is a fragmentary diagrammatic sectional view depicting a portion of the probe shown in FIG. 11.

FIG. 13 is a fragmentary diagrammatic sectional view depicting a further portion of the probe shown in FIG. 11.

FIG. 14 is a diagrammatic perspective view depicting a portion of the probe shown in FIG. 13.

DETAILED DESCRIPTION OF THE INVENTION

Figure 1:
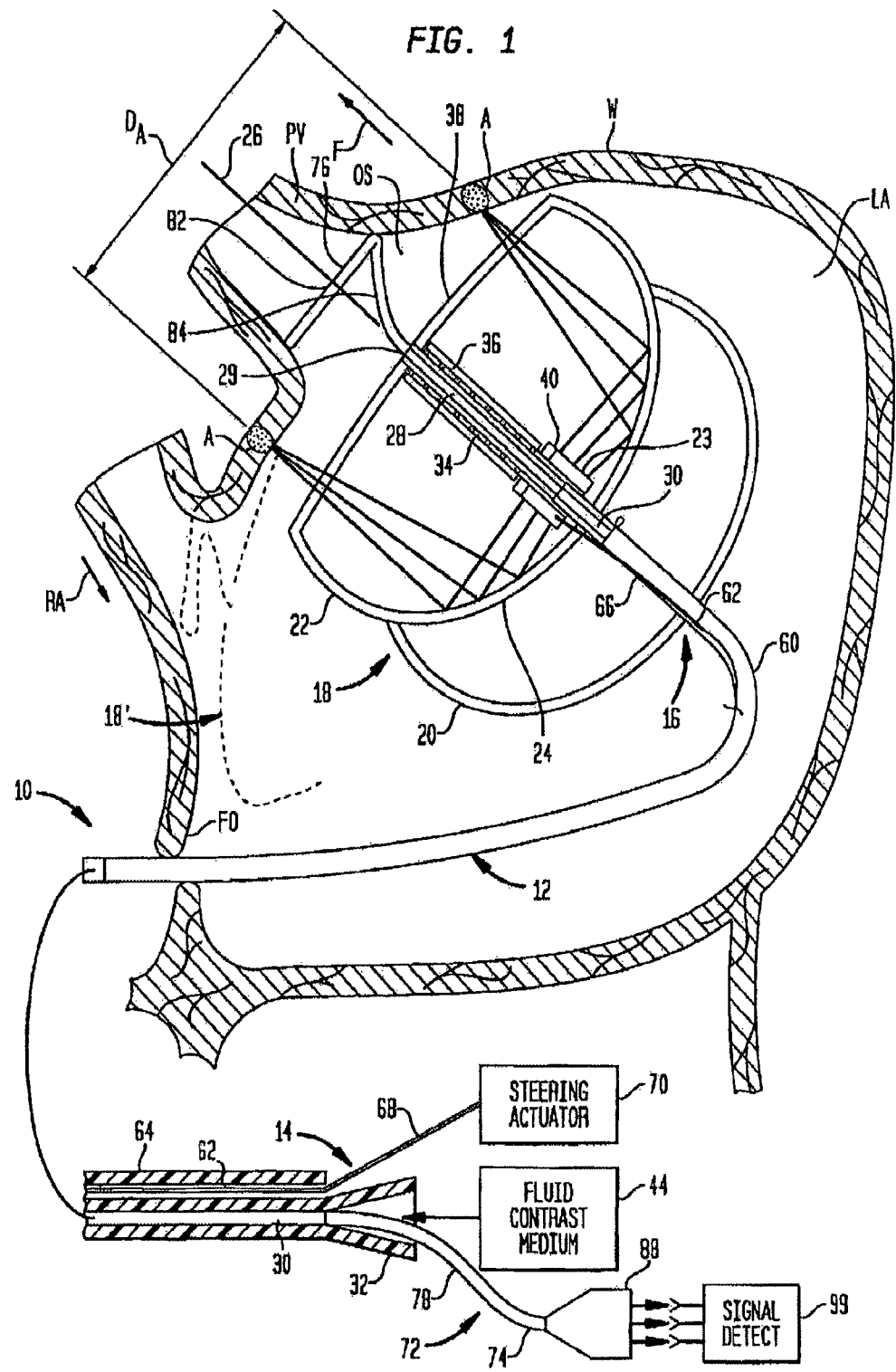
FIG. 1 is a diagrammatic, partial sectional view of apparatus showing an environment of this invention.

As seen in FIG. 1 (Cf, U.S. Pat. No. 8,398,623), apparatus relating to this invention includes an insertable structure 10 incorporating an elongated catheter 12 having a proximal end 14, which remains outside of the body, and a distal end 16 adapted for insertion into the body of the subject. As used in this disclosure with reference to structures which are advanced into the body of a subject, the "distal" end of such a structure should be taken as the end which is inserted first into the body and which penetrates to the greatest depth within the body, whereas the proximal end is the end of the structure opposite to the distal end. The insertable structure 10 also includes an ablation unit 18 mounted to the catheter adjacent distal end 16. Ablation unit 18 incorporates a reflector balloon 20 and a structural balloon 22 having a common wall 24. Reflector balloon 20 is linked to an inflation lumen (not shown) in catheter 10, which extends to the proximal end of the catheter and which is connected, during use, to a source of a gas under pressure, such as air or, more preferably, carbon dioxide, as, for example, to a gas-filled hypodermic syringe, so that the reflector balloon can be inflated with a gas. Structural balloon 22 is connected through a separate inflation lumen (not shown) to a source of a liquid such as isotonic saline solution, so that structural balloon 22 can be inflated with the liquid. A cylindrical ultrasonic emitter 23 is mounted within the structural balloon. Balloons 20 and 22, and particularly the common wall 24 separating the balloons, are designed so that in their inflated, operative condition illustrated in FIG. 1, the balloons are in the form of bodies of revolution about a central or forward-to-rearward axis 26. Emitter 23 is cylindrical and is coaxial with the balloons.

A tube defining a bore 28 extends through the structural balloon at the central axis 26. Tube bore 28 communicates with a port 29 on or forward of the forward wall 38 of the structural balloon. Tube bore 28 also communicates with a lumen 30 within catheter 12. Lumen 30 extends to the proximal end 14 of the catheter and is provided with a suitable fluid connection such as a Luer hub. Tube bore 28 and lumen 30 together form a continuous passageway extending from the outlet port 29, just distal to the ablation device back to the proximal end 14 of the catheter.

As also disclosed in the '524 patent, a coil spring 34 may be provided within the structural balloon, such that the coil spring surrounds tube 28. A reinforcing structure which may include one or more rigid tubes of metal or a rigid polymer such as polyether ether ketone ("PEEK") 36 extends coaxially with the tube defining bore 28 and spring 34. In the particular embodiment shown in FIG. 1, the rigid tubular structure 36 is disposed outside of tube spring 34; in other embodiments, the rigid tube or tubes can be disposed within spring 34, inside or outside of tube 28, so that the rigid tube or tubes define a portion of the bore. As described in greater detail in the '524 patent and in the aforementioned '757 application, the spring is compressed when the balloons are in the inflated, expanded state. When the balloons are deflated, the spring expands and moves the forward wall 38 of the structural balloon in the forward or distal direction F (up and to the left, as seen in FIG. 1) relative to the rearward or proximal end of the balloon and relative to the catheter 12, thereby collapsing the balloon in a radial direction, and also twists the balloons about axis 26 to facilitate radial collapse and formation of a small, radially compact unit for withdrawal from the patient. However, when the balloons are inflated, the spring is compressed and reinforcing element 36 engages a rigid mounting 40 attached to the distal end 16 of the catheter, which mounting also holds ultrasonic emitter 23. This assures that the axis 26 of the balloon structure is precisely aligned with the axis of the emitter and reinforces the balloon against deflection transverse to the axis 26.

In the arrangement depicted in FIG. 1, the tubular reinforcing element 36 abuts the distal end of the mounting 40. In a variant, the mounting is telescopically received within the tubular reinforcing element. Thus, as the balloons are inflated, the tubular reinforcing element 36 moves proximally or rearwardly so that the distal end of the mounting 40 enters into the tubular reinforcing element before the balloons are fully inflated. In the fully-inflated condition, the tubular reinforcing element remains slightly distal or forward of the transducer 23 or else abuts the distal end of the transducer. Engagement between the mounting and the reinforcing element helps prevent kinking or displacement of the structure transverse to axis 26 when the structure is in a partially-inflated or fully-inflated condition.

The common wall 24 separating the balloons forms an active, reflective interface. This active interface desirably has the form of a surface of revolution of a parabolic section around the central axis 26. When the balloons are in their inflated, expanded configuration shown in FIG. 1, ultrasonic waves emitted by emitter 23 are directed radially outwardly away from axis 26 and impinge on the parabolic active interface 24, where it is reflected forwardly and slightly outwardly away from axis 26 and focused so that the ultrasonic waves emitted along various paths mutually reinforces within a ring-like ablation region A, just forward of the forward wall 38 of the structural balloon encircling axis 26. The focused ultrasonic waves in this region can effectively ablate myocardial tissue and form a substantial conduction block extending through the heart wall in a relatively short time, typically about a minute or less.

Catheter 10 includes a bendable section 60. A steering mechanism is provided for selectively bending section 60 so as to orient the ablation device 18 and the forward-to-rearward axis 26 of the ablation device. In the particular embodiment depicted, the steering mechanism includes a pull wire 62 extending through a lumen 64, a portion of which is shown in FIG. 1. The pull wire has a distal end 66 affixed to the distal end 16 of the catheter, or to the ablation device itself. The proximal end 68 of the pull wire is connected to a handle or other appropriate device for manipulating the pull wire relative to the catheter. One particularly useful arrangement of the pull wire is further described in the aforementioned '757 application. By manipulating the pull wire, the bendable section 60 can be bent to a greater degree, or can be allowed to straighten. Also, the catheter structure desirably is "torquable," so that rotation applied to the catheter structure about its own axis at the proximal end is transmitted through the catheter to the distal end. Thus, the bendable section 60 can be rotated so as to change the orientation of the bendable section and, thus, the orientation of axis 26. The pull wire arrangement is merely exemplary of the numerous structures which can be used to provide steerability to the catheter.

Figure 2:
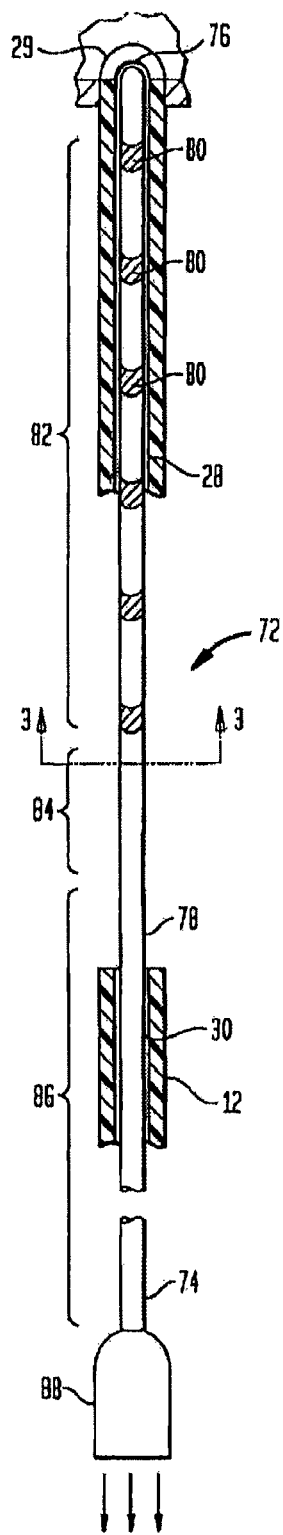
FIG. 2 is a fragmentary, diagrammatic perspective view depicting components of the apparatus shown in FIG. 1.

The apparatus further includes an elongated sensor probe 72 having a proximal end 74 and a distal end 76 (best seen in FIG. 2). The probe includes an elongated resilient body 78 having a diameter smaller than the inside diameter of lumen 30. A plurality of electrodes 80 (FIGS. 2 and 4) extend around the probe body in an operative region 82 adjacent the distal end of the probe, also referred to as a "hoop region." The probe body also includes a juncture region 84 disposed proximal to the operative region and a main or base region 86 extending from the juncture region to the proximal end 74 of the probe. A connector or coupler 88 is provided at the proximal end of the probe. As best seen in FIG. 3, the probe body 78 includes a dielectric layer 90 and conductors 92 extending within the dielectric layer from electrodes 80 to connector 88 (FIG. 2). The probe body also includes a resilient metallic element 94 extending along the length of the probe body. Element 94 may be a super elastic material such as an alloy of nickel and titanium, commonly referred as nitinol. The particular arrangement depicted in FIG. 3, with conductors 92 disposed around resilient element 94, is not essential. For example, the conductors may be grouped to one side of the elastic element. P robe 72 can be placed into the continuous passageway defined by the catheter lumen 30 and bore 28, and can be removed therefrom.

Figure 4A:
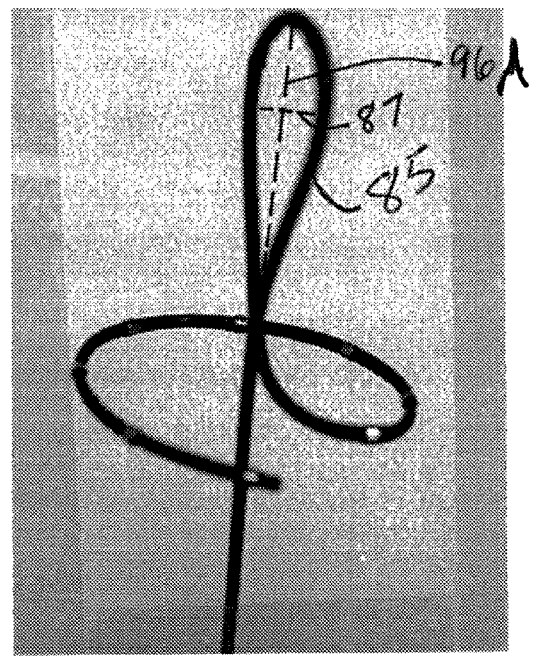
FIG. 4A is a photograph of a device of this invention schematically shown in FIG. 4.

In its free or unconstrained condition, probe body 78 assumes the shape depicted in FIG. 4. In this shape, hoop region 82 forms a generally circular hoop 82 in a plane generally transverse to the axis 96 defined by, and axially extending from, the distal-most part of main portion 86. The hoop encircles axis 96 and probe body 78 and is substantially coaxial therewith. The connecting limb or transition region 84 extends axially along axis 96 and defines an elongate, generally elliptical, or reverse loop 85. Loop 85 provides needed flexibility or strain relief to the transition region so that in a unconstrained state hoop 82 tends to center itself in hoop 82. Loop 85 has a major axis 96A which is substantially coaxial with axis 96 and a minor axis 87 which is substantially perpendicular thereto. Loop 85 permits resilient body 78 essentially to pass axially through the center of hoop region 82, with hoop region 82 being largely equidistant from body 78. A photograph of the structure shown in FIG. 4 is seen at FIG. 4A.

Figure 4B:
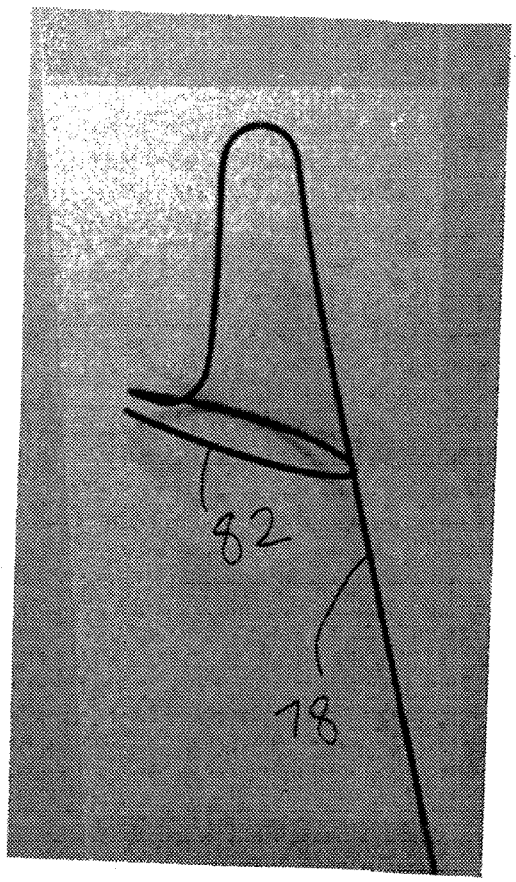
FIG. 4B is a device described in U.S. Pat. No. 8,398,623, incorporated by reference herein, constructed according to its teachings.

FIG. 4B shows a device described in U.S. Pat. No. 8,398,623 ("the '623 patent"). As can be seen, the extremely short, "shepherd's crook", connecting region 96 of the device described in the '623 patent (See, '623 patent, FIG. 6, and FIG. 4B), when constructed, causes or biases the probe body 78 to be displaced from the center of hoop region 82. The present invention overcame the disadvantage of the device of the '623 Patent. As discussed below, the probe body is in this unconstrained state when deployed within the heart, and accordingly, this condition is also referred to herein as the "deployed" condition of the probe body.

Figure 4C:
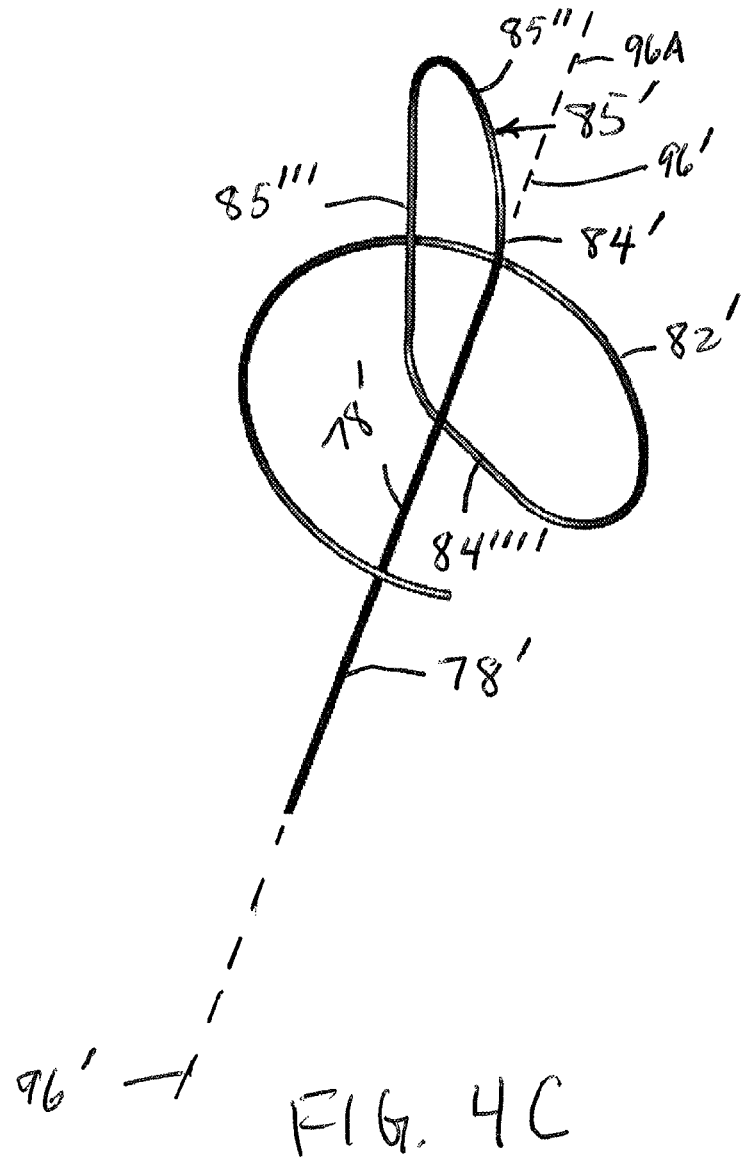
FIG. 4C is a further diagrammatic perspective view of a reverse loop ablation device of this invention in which much of the catheter structure (including sensors) has been removed for clarity.
Figure 9:
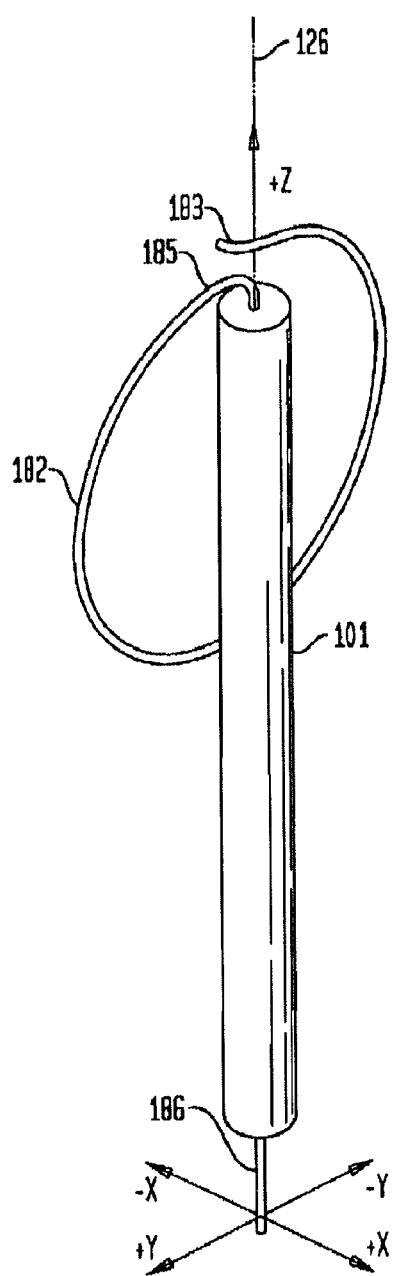
Figure 10:
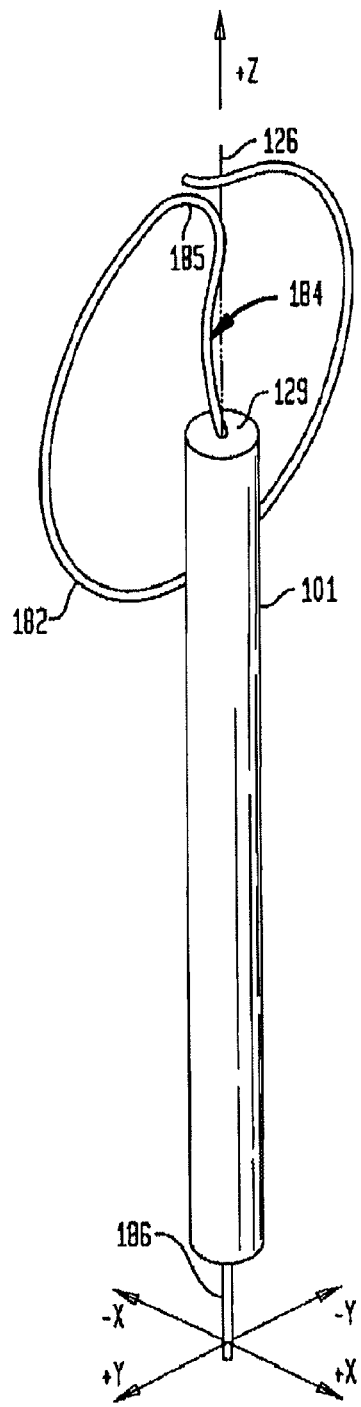

FIG. 4C is a further diagrammatic perspective view of a reverse loop ablation device of this invention in which much of the catheter structure (including the sensors) has been deleted for clarity. Loop 85' projects axially from probe body 78', and is defined by an ascending loop portion 85'' and a descending loop portion 85'''. Descending loop portion 85''' connects to loop 82' which defines a plane generally perpendicular to the axis 96' of probe body 78'. As is shown, descending loop portion 85''' passes behind probe body 78' and couples to loop 82' through radial segment 84''''.

In a method according to one aspect of the present invention, the ablation device 18 is positioned within a chamber of the heart as, for example, within the left atrium LA of a subject to be treated. A guide sheath (not shown) is advanced through the venous system into the right atrium and through the septum separating the right atrium and left atrium, so that the guide sheath provides access to the left atrium. Typically, the apparatus is advanced through the guide sheath with the balloons in a deflated, collapsed condition. This operation may be performed by first advancing a guide wire (not shown) into the heart, and then advancing the insertable structure 10, with the balloons in a deflated condition, over the guide wire. During this operation, probe 78 is not present in tube bore 28 and lumen 30. The guide wire passes through tube bore 28 and through lumen 30. A guide sheath also may be used during the insertion process.

When the ablation device 18 is disposed inside the heart chamber, the physician manipulates the device using steering mechanism 70 (FIG. 1) to vary the orientation of the ablation device, and hence the orientation of forward-to-rearward axis 26, until the device is positioned in the desired spatial relationship to the heart, with the axis 26 extending generally normal to the surface of the heart surrounding the ostium OS of a pulmonary vein PV.

In application, the physician may verify the proper disposition of the ablation device relative to the heart, by injecting a fluid contrast medium through the continuous passageway defined by lumen 30 and tube bore 28 and out through port 29 on the distal or forward side of the ablation device. Depending upon the pressure with which the contrast medium is injected, some portion of the contrast medium may pass into the pulmonary vein and other portions may remain within the left atrium. While the contrast medium is present, the subject is imaged using an imaging modality which will show the contrast medium as, for example, conventional x-ray or fluoroscopic imaging.

With the ablation apparatus properly positioned for ablation, the physician may actuate ultrasonic emitter 23, as by actuating an electrical energy source (not shown) connected to the emitter 23 by conductors in catheter 30 (also not shown). The ultrasonic emitter directs ultrasonic energy onto the wall 24 between balloons 20 and 22, where the energy is reflected in a forward direction F and focused into the ring-like ablation region A. The focused ultrasonic energy heats and ablates the myocardial tissue in this region, thereby converting this tissue into scar tissue which is not capable of conducting electrical impulses. Other ablation procedures, e.g., cryoablation are contemplated by this invention.

The physician may detect electrical signals within the pulmonary vein or pulmonary vein ostium by inserting probe 78 into the subject through the continuous passageway defined by lumen 30 and tube bore 28. The physician manually straightens the hoop region 82 and transition portion 84 as these are inserted through the proximal end of the catheter. The probe body has sufficient flexibility so that it can be advanced distally through the passageway. As the probe body advances through the catheter, the curvature of the probe body conforms to the existing curvature of the catheter. As the probe body continues to advance, it reaches the condition shown in FIG. 2. In this undeployed condition, the hoop region 82, transition region 84 and main region 86 are disposed in the continuous passageway, with the distal end 76 of the probe body proximal to port 29. As the physician continues to advance the sensor probe, the distal end 76, hoop region 82 and transition region 84 pass distally out of port 26, whereupon the hoop region and transition region spring back to their unconstrained or deployed shape, as depicted in FIG. 4. This places the hoop 82 concentric with the axis 96 defined by main portion 86 of the probe body. However, because the main portion 86 is disposed within the tube bore 28 of the ablation device, the main portion 86 is coaxial with the axis 26 of the ablation device. Thus, hoop 82 tends to deploy in a plane perpendicular to axis 26 of the ablation device, with the hoop concentric with the same axis. As mentioned above, during placement of ablation device 18, the physician has already positioned this axis in alignment with the pulmonary vein ostium and has positioned this axis generally normal to the plane of the heart tissue encircling the ostium. Thus, the hoop tends to deploy in a location as shown in FIG. 1, with the hoop lodged within the pulmonary vein ostium, or (depending upon the diameter of the pulmonary vein) in the pulmonary vein itself, and with the hoop 82 lying in the plane transverse to the axis of the pulmonary vein and the axis of the pulmonary vein ostium. All of this is accomplished without substantial manipulation by the physician to aim or locate the hoop. Stated another way, the ablation device 18 and catheter 12 act as an introducer structure which directs the distal portion of the sensor probe into alignment with the pulmonary vein ostium. Thus, placement of the sensor probe can be accomplished readily.

Although the catheter and ablation device act to introduce and aim the hoop region of the sensor, the hoop region is not rigidly mounted to the ablation device or catheter, and hence, is not rigidly positioned by these devices. Transition region 84 has some flexibility, so that the hoop 82 can be displaced or tilted somewhat from perfect coaxial alignment with the ablation device. This allows the hoop region to engage the tissues substantially around the pulmonary vein or ostium, even where these anatomical features are not perfectly aligned with the axis of the ablation device. Also, hoop 82 has some flexibility, and accordingly can conform to these structures, even where the same are not perfectly circular.

With the hoop 82 engaged with the tissues, electrodes 80 on the hoop will also be engaged with the tissues and hence will receive electrical signals propagating within the tissues. The physician can monitor these electrical signals using a conventional signal detection system 99 connected to connector 88 and hence connected to the electrodes through the conductors 92 (FIG. 3) of the sensor probe. If these electrical signals indicate that abnormal conduction is continuing to occur, the physician can actuate the ablation device again. The sensing probe need not be removed from the device during such further ablation. Alternatively, the sensing probe may be removed and other procedures, such as injection of additional contrast medium to confirm the desired disposition of the ablation device, may be performed. In a further variant, the sensor probe may be introduced and placed as described above before actuation of the ablation device, most typically after correct placement of the ablation device has been confirmed, as by use of the contrast medium technique discussed above.

In a further variant, the ablation device 18 can be repositioned to a new position as partially depicted in broken lines at 18' in FIG. 1. The sensor probe may be retracted into the catheter and ablation device, or may be entirely removed during the repositioning step. The same steps as discussed above may be repeated. The ability to retract or entirely remove the sensor probe facilitates repositioning. For example, contrast medium may be injected again to confirm the moved position of the apparatus. Also, because the sensor probe, does not project from the apparatus during the repositioning, step, it does not interfere with repositioning.

The sequence of operations used to deploy the sensor probe of FIGS. 4, 4A and 4B is depicted schematically in FIGS. 5-10. In these figures, the introducing structure, including the catheter and ablation device shown in FIG. 4 are symbolized by a generalized body 101. Also, the description uses a coordinate system with mutually orthogonal X, Y and Z directions. This coordinate system is associated with the main portion 186 of the probe body. Rotation of the main portion of the probe body about its own axis and about the axis 126 defined by the ablation device has no effect on the operations discussed with reference to FIGS. 5-10. As the probe body is advanced out through port 129, the leading end of the probe body is that portion which will ultimately form the tip 183 of the hoop region discussed above. This leading portion has a natural or unconstrained curvature relative to the next-trailing portion in a first or −X radial direction, in the X-Z plane, and thus deflects toward the −X axis when the probe is first advanced out through the port 129, as depicted in FIG. 7. The next part of the probe, hoop region 182 has a free or unconstrained curvature in the Y-Z plane, orthogonal to the curvature of portion 183. Thus, as hoop region 182 is progressively advanced out of port 129 {FIGS. 6 and 7), it curves relative to structure 101 and relative to the trailing portions of the probe body in the Y-Z plane, and thus first swings the leading tip portion in the +−Y direction, away from axis 126 and introducer structure 101, so that the tip portion moves generally in the +−Y direction. However, as more of portion 182 is advanced out of the port, the curvature of the hoop region causes the tip portion 183 to move generally in the opposite, −Y direction (FIG. 8), back towards axis 126 and introducer structure 101, until the tip portion 183 engages the introducer structure 101.

Because the tip portion 183 is curved in the −X direction, it provides a "lead-in" so that as tip 183 is urged further in the −Y direction by the deploying hoop region 182, tip portion 183 will tend to slide on the introducer structure 101 in the −X direction. Thus, as the hoop region 182 is further deployed, it will reliably pass on the −X side of introducer structure 101 and axis 126, so that the structure reaches the condition depicted in FIG. 9, with the juncture 185 of the hoop region and limb portion emerging from port 129. In this condition, hoop region 182 has formed a ring or hoop, with a portion of the hoop opposite from juncture 185 and tip portion 183 disposed on the −X side of the introducer structure 101.

As the limb portion 184 emerges from port 129, the loop travels in the +Z direction (FIG. 10) until the juncture between limb portion 184 and base portion 186, at the distal end 187 of the base portion, begins to emerge from the port. The curvature of the juncture at the distal end 187 of the base portion swings the limb portion in an arc in the Y-Z plane, so that the juncture 185 of the limb portion and hoop region 182 first moves in the +X direction and in the −Z or rearward direction. As the juncture 187 at the distal end of base portion 186 continues to emerge from the port, continued movement swings juncture 185 and hoop 182 in the −X direction, as well as in the −Z or rearward direction, as seen in FIG. 12. This action brings the hoop region 182 to the fully deployed condition depicted in FIGS. 4, 4A and 4B.

During deployment of the sensor probe discussed with reference to FIGS. 5-10, the expansible inflation device 118 may be temporarily retracted in the proximal or rearward direction relative to the wall of the heart, so as to provide clearance for movement of the hoop forward of the structure.

Numerous variations and combinations of the features discussed above can be utilized without departing from the present invention. Merely by way of example, it is not essential that the ablation device include the ultrasonic element and reflectors discussed above. For example, an expandable balloon having electrodes suitable for ablation or arrangements for delivering optical energy may be used. Also, the probe and method of probe deployment discussed above with reference to FIGS. 5-13 may be used for purposes other than sensing electrical signals in the context of an ablation process. For example, the probe can be used in a cardiac mapping operation, distinct from an ablation process. In a further variant, the functional elements of the probe (the sensing electrodes 180) may be used as ablation electrodes; or may be replaced by functional elements other than electrodes as, for example, discrete ultrasonic transducers or the like for an ablation process; or by sensors other than electrodes as, for example, chemical sensors. Further, although the present invention is particularly useful in performing procedures within the heart, it can be applied to performing procedures within other internal organs of a human or animal subject, or indeed, to performing procedures within a cavity of an inanimate subject.

A sensor probe in accordance with a further embodiment of the invention has a composite body 200 (FIG. 11.) including a tubular metallic shaft section 202 which may be formed from a stainless steel tube of the type commonly used, to form hypodermic needles. The shaft section defines interior bore 203 (FIG. 12). Desirably, the shaft section has an outside diameter $D_s$ (FIG. 12) on the order-of 1.25 mm or less, more desirably about 1 mm (0.040 inches) or less, and most preferably about 0.9 mm (0.035 inches). Preferably, the shaft section 202 extends throughout the majority of the length of the probe 200. For example, the shaft section may be on the order of 140 cm (55 inches) long.

A distal section 206 is mounted to the distal end 204 of shaft section 202. The distal section 206 includes a wire core 210 (FIG. 13) with a dielectric; biologically inert polymeric covering 212 overlying the core. The core desirably is formed from a metal such as a nickel-titanium alloy which can be formed to a preselected shape and which will tend to return to the preselected shape when unconstrained. A plurality of electrodes 216 overlie the covering 212 in a portion of the length of the distal section. As best seen in FIG. 11, this portion 208 of the distal section in its free or unconstrained condition forms a hoop lying in a plane transverse to the axis defined by the remainder of the distal section. In the free or unconstrained condition, the distal section may extend about 5 cm (2 inches) proximally from the plane of the hoop. The distal section 206 is formed to this hoop shape and tends to return to this shape when the distal section is unconstrained. However, the distal section is quite flexible, and hence, can be constrained to a straight or gently curving shape, so as to be advanced through the passageway defined by the catheter and ablation device as discussed above. Shaft section 202 is flexible enough to pass through gently curving portions of the catheter, but is considerably stiffer than the distal section.

The proximal end of the distal section 206 abuts the distal end 204 of the shaft section and is bonded to the shaft section 202. Desirably, wire core 210 extends into the bore 203 of the shaft section a short distance from this abut joint. A plurality of fine insulated wires 220 are disposed within the bore 203 of the shaft section. These wires are electrically connected to electrodes 216 on the distal section. The probe body also includes a proximal section 222 and a transition section 224 extending from the proximal section to the proximal end 226 of the shaft portion. The proximal end section may include a relatively stiff polymeric tube having an interior bore (not shown). The transition section 224 may include a polymeric tube having stiffness intermediate between that of the proximal end section and the shaft section; this tube also having an interior bore. The interior bores of the transition section 224 and proximal section 222 may communicate with the bore of shaft section 202. Alternatively, the metallic tube forming shaft section 202 may extend through the interior bores of the transition section and the proximal section. In either arrangement, wires 220 may extend all the way to the proximal end of proximal end section 222. An electrical connector 230 is connected to these wires and, hence, to electrodes 216.

In use, the probe body according to this embodiment can be advanced and deployed as discussed above. The shaft portion 202 constituting the major portion of the probe length has an appreciable stiffness. Moreover, the shaft portion is smooth and slides readily within the structures defining the passageway. Therefore, the probe does not tend to buckle and jam as the probe is threaded through the passageway of the catheter. During threading, of course, the distal end portion is not in the hoop-shape shown, but instead is straight or slightly curved to match the curvature of the passageway in the catheter. Typically, the distal end portion 206 is substantially more flexible than the shaft portion 202. The joint between the distal end portion and the shaft portion (at the distal end 204 of the shaft portion) most preferably lies just proximal to the bendable section 62 of the catheter when the probe is fully advanced.

As these and other variants can be employed, the foregoing description of the preferred embodiments should be taken by way of illustration rather than by way of limitation of the invention as further set forth in the claims.

What is claimed is as follows:

1. An apparatus for cardiac treatment, the apparatus comprising:
 a) a catheter having a catheter passageway extending to a proximal catheter end and a distal catheter portion having a distal catheter end provided with a port;
 b) an elongated sensor probe comprising a probe body residing along a longitudinal axis and extending to a reverse loop, at least a portion of the reverse loop residing along an imaginary plane that intersects the longitudinal axis, wherein the reverse loop consists of an ascending loop portion at least partially residing on the imaginary plane spaced from the longitudinal axis in a first direction and extending to a peak of the loop intersecting the longitudinal axis, the peak of the loop extending to a descending loop portion at least partially residing on the imaginary plane spaced from the longitudinal axis in a second direction, opposite the first direction, with the descending loop portion then extending to a partially circular hoop; and
 c) at least one sensing electrode disposed on the partially circular hoop of the sensor probe,
 d) wherein the sensor probe is movable along the catheter passageway and out the catheter port so that, in a deployed position, the probe body resides inside the partially circular hoop and the partially circular hoop resides in a plane that is substantially transverse to the longitudinal axis of the probe body.

2. The apparatus of claim 1, wherein the reverse loop of the sensor probe is elliptical.

3. The apparatus of claim 1, wherein, in the deployed position, the reverse loop has a major loop axis and a minor loop axis, the minor loop axis being aligned substantially perpendicular to the major loop axis, and wherein the major loop axis of the reverse loop portion is substantially coaxial with the longitudinal axis of the probe body.

4. An apparatus for cardiac treatment, the apparatus comprising:
 a) a catheter having a catheter passageway extending to a proximal catheter end and a distal catheter portion having a distal catheter end provided with a port;
 b) an elongated sensor probe comprising a probe body residing along a longitudinal axis and extending to an elliptical reverse loop at least partially residing along a first imaginary plane that intersects the longitudinal axis, wherein the reverse loop consists of an ascending loop portion at least partially residing on the first imaginary plane spaced from the longitudinal axis in a first direction and extending to a peak of the loop intersecting the longitudinal axis, the peak of the loop extending to a descending loop portion at least partially residing on the first imaginary plane spaced from the longitudinal axis in a second direction, opposite the first direction, with the descending loop portion then extending to a partially circular hoop;
 c) at least one sensing electrode disposed on the partially circular hoop of the sensor probe; and
 d) an expansible ablation device mounted to the catheter distal portion at a location proximal the port, the expansible ablation device comprising:
  i) an ultrasonic emitter; and
  ii) a proximal reflector balloon connected to a distal structural balloon at a common wall,
  iii) wherein, in an expanded condition with the reflector balloon inflated with a gas and the structural balloon inflated with a liquid, the common wall is configured to direct ultrasonic energy from the emitter and into a loop-like region bounded by the partially circular hoop of the sensor probe, and
 e) wherein the sensor probe is movable along the catheter passageway and out the catheter port so that, in a deployed position, the probe body resides inside the partially circular hoop and the partially circular hoop resides in a second imaginary plane that is adjacent to the catheter port and substantially transverse to the longitudinal axis of the probe body.

5. The apparatus of claim 4, wherein the descending loop portion passes behind the probe body and extends to the partially circular hoop.

6. The apparatus of claim 4, wherein, with the expansible ablation device in the expanded condition with the reflector balloon inflated with a gas and the structural balloon inflated with a liquid, the common wall formed by the proximal reflector balloon connected to the distal structural balloon is reflective to ultrasonic energy.

7. The apparatus of claim 6, wherein, with the expansible ablation device in the expanded condition with the reflector balloon inflated with a gas and the structural balloon inflated with a liquid, the common wall formed by the distal structural balloon connected to the proximal reflector balloon faces the loop-like region bounded by the partially circular hoop of the sensor probe.

8. The apparatus of claim 7, wherein, when the partially circular hoop extends outwardly from the catheter port, the partially circular hoop is coaxial with the longitudinal axis of the probe body.

9. The apparatus of claim 5, wherein the distal structural balloon includes a distal wall, and wherein, with the expansible ablation device in the expanded condition with the reflector balloon inflated with a gas and the structural balloon inflated with a liquid, the loop-like region is aligned substantially parallel to an imaginary plane aligned with the distal wall of the structural balloon.

10. The apparatus of claim 9, wherein, with the expansible ablation device in the expanded condition with the reflector balloon inflated with a gas and the structural balloon inflated with a liquid, the catheter port is aligned in a substantially coplanar relationship with the distal wall of the structural balloon.

11. The apparatus of claim 5, wherein the partially circular hoop of the sensor probe is substantially coaxial with the loop-like region.

12. The apparatus of claim 9, wherein, with the expansible ablation device in the expanded condition with the reflector balloon inflated with a gas and the structural balloon inflated with a liquid, the partially circular hoop of the sensor probe is aligned in a substantially coaxial relationship with the distal wall of the structural balloon.

13. The apparatus of claim 9, wherein, with the expansible ablation device in the expanded condition with the reflector balloon inflated with a gas and the structural balloon inflated with a liquid, the catheter port is aligned in a substantially coplanar relationship with the distal wall of the structural balloon, and the partially circular hoop is aligned substantially parallel to an imaginary plane aligned with the distal wall.

14. The apparatus of claim 4, wherein the catheter includes a bendable section that is adjacent to the distal end of the catheter, but proximal to the expansible ablation device.

15. The apparatus of claim 4, further comprising one or more pull wires, each pull wire having a distal end connected to the catheter at a position that is distal to the bendable section or to the expansible ablation device, wherein the one or more pull wires are slidably mounted to the catheter so that the bendable section of the catheter can be selectively bent by pulling the one or more pull wires in a proximal direction.

16. The apparatus of claim 4, wherein the sensor probe includes a tubular metallic shaft section and a distal section connected to a distal end of the metallic shaft section, the distal section of the sensor probe including the partially circular hoop carrying the at least one sensing electrode, wherein the sensor probe further comprises at least one conductor extending within the shaft section and being electrically connected to the at least one sensing electrode.

17. The apparatus of claim 16, wherein the distal section of the sensor probe comprises a wire core, a polymeric covering overlying the wire core, and wherein the at least one sensing electrode overlays the polymeric covering so that the covering insulates the sensing electrode from the wire core.

18. The apparatus of claim 16, wherein the metallic shaft section and the distal section have cross-sectional dimensions of greater than zero up to about 1.25 mm.

19. The apparatus of claim 16, wherein there are a plurality of electrodes disposed on the partially circular hoop of the sensor probe.

20. The apparatus of claim 16, wherein the distal section of the sensor probe is more flexible than the metallic shaft section.

21. The apparatus of claim 4, wherein the reverse loop has a major loop axis and a minor loop axis, the minor loop axis being aligned substantially perpendicular to the major loop axis.

22. The apparatus of claim 21, wherein, in the deployed position, the major loop axis of the reverse loop is substantially coaxial with the longitudinal axis of the probe body.

23. An apparatus for cardiac treatment, the apparatus comprising:
   a) a catheter having a catheter passageway extending to a proximal catheter end and a distal catheter portion having a distal catheter end provided with a port;
   b) an elongated sensor probe comprising a probe body residing along a longitudinal axis and extending to a reverse loop, wherein the reverse loop consists of an ascending loop portion spaced from the longitudinal axis in a first direction and extending to a peak of the loop intersecting the longitudinal axis, the peak of the loop extending to a descending loop portion spaced from the longitudinal axis in a second direction, opposite the first direction, with the descending loop portion then extending to a partially circular hoop; and
   c) at least one sensing electrode disposed on the partially circular hoop of the sensor probe,
   d) wherein the sensor probe is movable along the catheter passageway and out the catheter port so that, in a deployed position, the probe body resides inside the partially circular hoop and the partially circular hoop resides in a plane that is substantially transverse to the longitudinal axis of the probe body.

* * * * *